United States Patent [19]
Olbrich et al.

[11] Patent Number: 4,926,005
[45] Date of Patent: May 15, 1990

[54] DEHYDROGENATION PROCESS

[75] Inventors: Michael E. Olbrich, Lake Jackson, Tex.; Dwight L. McKay, Bartlesville, Okla.; Dean P. Montgomery, deceased, late of Washington County, Okla.; by B. Jean, administratrix Montgomery, Bartlesville, Okla.

[73] Assignee: Phillips Petroleum Company, Bartlesville, Okla.

[21] Appl. No.: 353,849

[22] Filed: May 17, 1989

[51] Int. Cl.$^5$ ............................................. C07C 5/327
[52] U.S. Cl. .................................. 585/632; 585/654
[58] Field of Search ............................. 585/632, 654

[56] References Cited

U.S. PATENT DOCUMENTS

| | | | |
|---|---|---|---|
| 3,491,162 | 1/1970 | Bloch et al. | 260/671 |
| 3,641,182 | 2/1972 | Box, Jr. et al. | 260/680 R |
| 3,670,044 | 6/1972 | Drehman et al. | 260/683.3 |
| 3,761,539 | 9/1973 | Drehman et al. | 260/683.3 |
| 3,880,776 | 4/1975 | Box, Jr. et al. | 252/466 PT |
| 3,894,110 | 7/1975 | Drehman | 260/680 R |
| 3,904,703 | 9/1975 | Lo et al. | 260/669 R |
| 3,957,688 | 5/1976 | Farha et al. | 252/455 R |
| 4,152,365 | 5/1979 | Drehman | 585/256 |
| 4,613,715 | 9/1986 | Haskell | 585/412 |

Primary Examiner—Patrick P. Garvin
Assistant Examiner—George R. Fourson
Attorney, Agent, or Firm—K. K. Brandes

[57] ABSTRACT

In a process for dehydrogenating alkanes having 2-5 carbon atoms per molecule in the presence of steam and a catalyst composition comprising Group IIA and/or IIB metal aluminate, Group VIII metal(s) and Group IVA metal compound(s), the improvement comprises the step of pretreating the alkane containing feed with a material comprising a Group IIA and/or Group IIB metal aluminate under non-dehydrogenating conditions.

18 Claims, No Drawings

DEHYDROGENATION PROCESS

BACKGROUND OF THE INVENTION

This invention relates to a process for dehydrogenating light paraffins. In another aspect, this invention relates to the use of a promoted zinc aluminate catalyst in a dehydrogenation process.

It is known to dehydrogenate light aliphatic hydrocarbons in the presence of catalysts which compromise a Group II metal aluminate, a Group IVA metal oxide and a Group VIII metal. However, there is an ever present need to improve conversion and selectivity to desired products in dehydrogenation processes. The process of this invention is directed to attaining these improvements.

SUMMARY OF THE INVENTION

It is an object of this invention to dehydrogenate light parafins (alkanes) in the presence of a promoted Group II metal aluminate catalyst. It is another object of this invention to pretreat an alkane-containing feed in a dehydrogenation process, so as to enhance conversion and/or olefin yield. Other objects and advantages will become apparent from the disclosure and the appended claims.

According to the present invention, in a process comprising the step of dehydrogenating a feed stream comprising at least one alkane (paraffin) having from 2 to 5 carbon atoms per molecule, in the presence of steam and a catalyst composition comprising, at least one aluminate spinel selected from the group consisting of aluminates of Group IIA metals and Group IIB metals of the Periodic Table (defined in Webster's New Collegiate Dictionary, 1977, page 852), (ii) at least one Group VIII metal selected from the group consisting of nickel, ruthenium, rhodium, palladium, osmium, iridium and platinum, and (iii) at least one compound (preferably oxide) of a Group IVA metal selected from the group consisting of germanium, tin and lead, under such dehydrogenation conditions as to at least partially convert said at least one alkane to at least one alkene (monoolefin);

The improvement comprises a pretreating step which comprises passing the alkane-containing feed, prior to the above-described dehydrogenation step, through a fixed bed of a pretreating material comprising at least one aluminate spinel selected from the group consisting of Group IIA metal aluminates and Group IIB metal aluminates, under non-dehydrogenation conditions.

The pretreating step will result in an enhancement of alkane conversion and/or alkene yield in the dehydrogenation step, as compared with a dehydrogenation process without the pretreating step. The pretreating step is carried out at a temperature low enough that essentially no dehydrogenation of the feed alkane(s) occurs.

In a preferred embodiment, the alkane-containing feed stream is essentially free of added hydrogen gas and added oxygen gas, and consists essentially of at least one alkane. In another preferred embodiment, the aluminate spinel component of the catalyst composition is zinc aluminate, the Group VIII metal component of the catalyst composition is platinum, and the Group IVA metal oxide component of the catalyst composition is tin oxide (more preferably $SnO_2$). In a further preferred embodiment, the catalyst composition and the pretreating material contain the same components, i.e., components (i), (ii), and (iii).

DETAILED DESCRIPTION OF THE INVENTION

The dehydrogenation catalyst composition which is employed in the process of this invention can be prepared by any suitable method and in any suitable manner, such as those well known in the art. The preparation comprises combining, in any suitable manner, (i) a Group IIA metal aluminate spinel (i.e., aluminate spinel of Be and/or Mg and/or Ca and/or Sr and/or Ba) or a Group IIB metal aluminate spinel (i.e., aluminate spinel of Cd and/or Zn), or a mixture of two or more of the above Group IIA and IIB metal aluminate spinels; (ii) Group VIII metal and/or compound(s) thereof, and (iii) compound(s) of Ge and/or Sn and/or Pb.

Aluminate spinels, as referred to herein, are compounds of the formula $M(AlO_2)_2$ or $MOAl_2O_3$, wherein M is a metal of Group II or IIB of the Periodic Table (as defined in Webster's New Collegiate Dictionary, 1977, page 852) with a valence of 2, such as Zn, Mg, Be, Ca and the like. The preparation of these aluminate spinels as described in numerous patents, such as U.S. Pat. Nos. 3,641,182; 3,670,044; 3,880,776; 3,894,110; 3,957,688 and 4,152,365, the disclosures of which are herein incorporated by reference. In a preferred embodiment, tin oxide is incorporated into the aluminate spinel. In another preferred embodiment, component (i) comprises zinc aluminate as major component and calcium aluminate as binder (generally present at about 5-25 weight %).

In the presently preferred method of preparation, the metal aluminate is prepared by ball-milling appropriate amounts of zinc oxide and alumina and, optionally, tin oxide (SnO and/or $SnO_2$), and calcining (preferably by heating in air) the mixture at a sufficiently high temperature for a sufficient length of time to form the spinel. Preferably, the spinel component is used as support material, which is impregnated with component (ii) and with component (iii) in any suitable manner, either sequentially in any order or simultaneously, as has been described in the above-cited patents.

The components of the catalyst composition generally are present at the following levels: about 80-98 weight% of Group IIA and/or IIB metal aluminate spinel (preferably zinc aluminate); about 0.05-5 weight % of Group VIII metal (preferably Pt); and about 0.1-5 weight % Group IVA metal (preferably Sn, present as oxide). It is understood that additional components which are beneficial for catalyzing the dehydrogenation of saturated hydrocarbons may also be present in small amounts, such as Re, Au, Ag, alkali metal, Ce, and the like. Suitable inorganic binder materials (such as amorphous alumina) may also be present. Generally the surface area of the catalyst composition (after calcination) is in the range of from about 5 to about 100 $m^2/g$ (determined by nitrogen adsorption in accordance with the BET method).

Any suitable paraffin containing 2-5 C atoms per molecule (normal alkane or isoalkane or mixtures) can be used as feed in the dehydrogenation process of this invention. Non-limiting examples are ethane, propane, n-butane, isobutane, n-pentane, 2-methylbutane, and the like. Particularly preferred are propane, n-butane, and isobutane; most preferably isobutane.

The dehydrogenation conditions of the dehydrogenation step of the invention are well known and have been described in the above-cited patents. Steam is present to alleviate coke deposition on the catalyst, to enhance feed conversion, and to retard catalyst deactivation. The reaction temperature in the dehydrogenation step is considerably higher than the normal boiling temperature (measured at 1 atm.) of the feed alkane. The reaction temperature in the dehydrogenation step generally is in the range of from about 500° to about 650° C. The molar ratio (essentially equal to volume ratio) of steam to alkane in the vaporized feed generally is in the range of from about 0.5:1 to about 30:1 (preferably from about 2:1 to about 10:1). The pressure in the dehydrogenation step generally is in the range of from about 0 to about 200 psig, and preferably is about 20-100 psig.

In the dehydrogenation step of the process of this invention, generally a mixture of steam and vaporized alkane (at a suitable molar ratio, recited above) is preheated and passed through the dehydrogenation reactor (or a train of two or more reactors in series or in parallel) containing a fixed bed of the catalyst composition of this invention (which can be in any suitable form, such as granules, pellets, spheres and the like). The gas hourly space velocity of the vaporized alkane feed (excluding steam) in the dehydrogenation step generally is in the range of from about 100 to about 10,000 cc alkane per cc catalyst per hour, preferably from about 500 to about 2,000 cc/cc/hour. The flow rate of steam is determined by the desired volume ratio of steam to alkane feed (as disclosed above). Free oxygen is substantially absent during the dehydrogenation step of this invention since $O_2$ causes the formation of higher amounts of undesirable carbon oxides ($CO$ and/or $CO_2$) during the process.

The catalyst composition of this invention gradually loses some of its catalytic activity during the dehydrogenation step. When the catalytic activity has dropped below an effective level (generally after about 6-20 hours on stream), the flow of the alkane-containing feed is cut off, and a purge gas comprising steam and/or an inert gas (e.g., $N_2$, Ar, He) is passed through the hot catalyst bed (at a temperature of about 500°-650° C., for about 1-60 minutes), so as to substantially remove hydrocarbons from the reactor.

Subsequently, the catalyst composition is regenerated. The catalyst regeneration is preferably carried out by treating the catalyst for a suitable time with a stream of steam-diluted air, as is shown in U.S. Pat. No. 4,613,715, the disclosure of which is herein incorporated by reference. Generally, the regeneration temperature is in the range of from about 450° to about 750° C. (preferably about 500°-700° C.), and the molar ratio (volume ratio) of steam to free oxygen is in the range of from about 40:1 to about 200:1. The flow rate of steam during catalyst regeneration is approximately the same as in the dehydrogenation step. The pressure during the regeneration cycle generally is about 0-200 psig, preferably about 20-100 psig. The duration of the regeneration step depends on the regeneration conditions and on the amount of coke deposits to be removed. Generally, the regeneration step is carried out for about 0.1 to about 5 hours, preferably about 0.2-1 hour.

The pretreating step comprises passing the alkane-containing feed stream (without steam) through a fixed bed of the pretreating material at a temperature low enough that no dehydrogenation occurs. The alkane-containing feed can be liquid or gaseous, preferably gaseous. Generally the temperature in the pretreating step (i.e., the temperature of the feed and of the pretreating material) is in the range of from about −50° to about 400° C., preferably in the range of from about 0° to about 120° C., and more preferably in the range of from about 5° to about 100° C. The flow rate of the alkane-containing feed and the pressure in the pretreating step are essentially the same as in the dehydrogenation step (described above). The duration of the pretreating step (i.e., the time of contact of the feed with the pretreating material under non-dehydrogenation conditions) generally is about 0.01 to about 100 minutes, preferably about 0.1 to about 20 minutes.

The pretreating material can be unpromoted Group IIA and/or IIB metal aluminate, in particular zinc aluminate and/or calcium aluminate. Alternatively, the pretreating composition can also contain a Group IVA metal oxide, in particular tin oxide (preferably about 0.1-5 weight % Sn). Preferably, the pretreating material also contains Group VIII metal and is substantially the same as the dehydrogenation catalyst composition, described above. It is within the scope of this invention to employ a spent dehydrogenation catalyst composition, optionally after removal of at least a portion of Group VIII metal therefrom. When the pretreating material used in the pretreating step has become ineffective, it can be discarded and replaced by fresh material or it can be regenerated, i.e., by heating in a stream of air and/or steam and/or steam-diluted hydrogen and/or inert gas (e.g., He, $N_2$).

After the alkane-containing feed has exited from the fixed pretreating bed, the feed is passed to a feed preheater where the feed is heated to or close to the desired reaction temperature of the subsequent dehydrogenation step, before the feed is introduced into the dehydrogenation reactor. Steam is introduced concurrently with the alkane-containing feed stream into the reactor, or steam and the alkane-containing feed are mixed and are then introduced as a mixture into the dehydrogenation reactor. Preferably, the entire operation (pretreating, preheating, and dehydrogenation) is carried out continuously.

The product of the dehydrogenation process comprises primarily monoolefins (alkenes). By-products are $CO$, $CO_2$, diolefins, and possibly aromatics. When propane is used as feed, primarily propylene is formed; when n-butane is used, primarily butene-1 and butene-2 are formed; and when isobutane is used as feed, primarily isobutene is formed. When the pretreating step is carried out in accordance with this invention, alkane conversion and olefin yield attained in the dehydrogenation step are higher than in a comparable dehydrogenation step without the prior pretreating step. It is theorized (even though the inventors do not wish to be bound by this theory) that small amounts of impurities which poison the catalyst in the dehydrogenation step are removed in the pretreating step.

The formed monoolefinic hydrocarbons can be recovered after having been separated from other components of the reaction product mixture of the dehydrogenation process by any suitable means, such as fractional distillation (preferably at low temperature and high pressure), well known absorption/desorption processes, and membrane separation techniques. Unreacted hydrocarbon feed, after it has been substantially separated from reaction product components, can be recycled to the pretreating zone or to the dehydrogenation reactor which contains the catalyst composition.

The following examples are presented in further illustration of the invention and are not to be considered as unduly limiting the scope of this invention.

EXAMPLE

This example illustrates the dehydrogenation of isobutane over a promoted zinc aluminate catalyst, with and without prior contacting of the isobutane feed with a guard bed containing this catalyst.

Isobutane and steam were introduced into a pilot plant reactor having a length of about 2 feet and a diameter of about 2 inches. The reactor was filled with a layer (about 14 inches high) of about 780 cc (974 g) of a promoted zinc aluminate dehydrogenation catalyst, which was prepared substantially in accordance with the method described in Example I of U.S. Pat. No.4,152,365 and contained about 44.0 weight % ZnO, about 53.5 weight-% $Al_2O_3$, 1.3 weight-% $SnO_2$ and 0.6 weight % Pt.

Liquid isobutane was introduced into the reactor at a feed rate of 3077 cc/hr (1728 g/hr), and steam was introduced at a rate of about 2125 g/hr. Thus, the weight ratio of steam to isobutane was 1.23:1, and the molar ratio of steam to isobutane was 3.95:1. The liquid hourly space velocity of isobutane was 3.94 cc/cc catalyst/hour, which translated to a gas hourly space velocity at S.T.P. conditions of about 890 cc/cc catalyst/hour. The average temperature of the catalyst bed was about 1070° F., and the average reaction pressure was about 50 psig.

Generally, the mixture of isobutane and steam was passed through the reactor for 7 hours. Then the isobutane flow was discontinued, and the reactor was purged with steam (about 2100 g/minute) for 5–10 minutes. Thereafter, air was introduced into the reactor at a rate of about 10 standard cubic feet per hour (SCFH) for about 25 minutes, and then at a rate of about 20 SCFH for about 25 minutes, while the steam flow rate remained about 2100 g/hour, so as to regenerate the hot catalyst (i.e., to burn off coke deposits). Subsequently, the flow of air was discontinued, and a purge stream of steam was passed through the reactor for 5 minutes, before isobutane was introduced again for another dehydrogenation cycle.

In the two invention runs, the isobutane feed stream (without steam) was passed through a guard bed filled with about 560 g of the dehydrogenation catalyst described above, before the feed was heated and introduced into the dehydrogenation catalyst. The guard bed had approximately the same dimensions as the dehydrogenation reactor and was filled with about 450 cc of the dehydrogenation catalyst so as to provide a liquid hourly space velocity of the feed of 7 cc/cc catalyst/hour. The temperature in the guard bed was about 70°–80° F., and no dehydrogenation of the isobutane occurred in the guard bed. In the two control runs, the guard bed was by-passed, and the preheated isobutane feed was directly introduced into the dehydrogenation reactor. Pertinent test results are summarized in Table I.

TABLE I

| Run | Guard Bed | Average Isobutane Conversion (%) | Average Selectivity to Isobutene (%) | Average Isobutene Yield (%) |
|---|---|---|---|---|
| 1 (Invention) | Yes | 53.1 | 89.9 | 47.7 |
| 2 (Control) | No | 50.9 | 91.4 | 46.5 |
| 3 (Invention) | Yes | 51.8 | 93.8 | 48.6 |
| 4 (Control) | No | 49.9 | 93.9 | 46.9 |

Data in Table I indicate that passing the isobutane feed through a guard bed of the dehydrogenation catalyst at room temperature had a beneficial effect on isobutane conversion and isobutane yield attained in the subsequent dehydrogenation step. Additional test results (not listed in Table I) indicate that the rate of the decline of isobutane conversion during a 7 hour dehydrogenation run was about 20% less in invention runs 1 and 3 than in control runs 2 and 4.

Reasonable variations, modifications and adaptations for various usages and conditions can be made within the scope of the disclosure and the appended claims, without departing from the scope of this invention.

That which is claimed is:

1. In a process comprising the step of dehydrogenating a feed stream comprising at least one alkane having from 2 to 5 carbon atoms per molecule, in the presence of steam and a dehydrogenation catalyst composition comprising (i) at least one aluminate spinel selected from the group consisting of Group IIA metal aluminates and Group IIB metal aluminates, (ii) at least one metal selected from the group consisting of nickel, ruthenium, rhodium, palladium, osmium, iridium and platinum, and (iii) at least one compound of a metal selected from the group consisting of germanium, tin and lead, under such dehydrogenation conditions as to at least partially convert said at least one alkane to at least one alkene;

the improvement comprising a pretreating step which comprises passing said feed stream, prior to said step of dehydrogenating, through a fixed bed of a pretreating material comprising at least one aluminate spinel selected from the group consisting of Group IIA metal aluminates and Group IIB metal aluminates, under non-dehydrogenation conditions.

2. A process in accordance with claim 1, wherein said pretreating material is selected from the group consisting of zinc aluminate, calcium aluminate and mixtures thereof.

3. A process in accordance with claim 1, wherein said pretreating material additionally comprises at least one oxide of a metal selected from the group consisting of germanium, tin and lead.

4. A process in accordance with claim 3, wherein said pretreating material additionally comprises at least one metal selected from the group consisting of nickel, ruthenium, rhodium, palladium, osmium, iridium and platinum.

5. A process in accordance with claim 1, wherein said pretreating material comprises (i) at least one metal aluminate selected from the group consisting of zinc aluminate and calcium aluminate, (ii) platinum metal, and (iii) tin oxide.

6. A process in accordance with claim 5, wherein said pretreating material comprises about 0.05 to about 5 weight % Pt and about 0.1 to about 5 weight % Sn, present as tin oxide.

7. A process in accordance with claim 1, wherein said pretreating material is a spent dehydrogenation catalyst composition.

8. A process in accordance with claim 1, wherein said pretreating step is carried out at a temperature in the range of from about $-50°$ to about $400°$ C.

9. A process in accordance with claim 8, wherein said temperature is in the range of from about 0 to $120°$ C.

10. A process in accordance with claim 8, wherein said pretreating step is carried out for about 0.01 to about 100 minutes.

11. A process in accordance with claim 1, wherein said at least one alkane is selected from the group consisting of propane, n-butane and isobutane.

12. A process in accordance with claim 1, wherein said catalyst composition comprises zinc aluminate, platinum, and tin oxide.

13. A process in accordance with claim 1, wherein said catalyst composition comprises about 0.5–5 weight % Pt and about 0.1–5 weight % Sn, present as tin oxide.

14. A process in accordance with claim 1, wherein said dehydrogenation conditions comprise a temperature in the range of from about 500 to about $650°$ C and a molar ratio o: steam to alkane in the range of from about 0.5:1 to about 30:1.

15. A process in accordance with claim 1, wherein said dehydrogenation conditions comprise the substantial absence of free oxygen.

16. A process in accordance with claim 1 comprising the additional steps of discontinuing the flow of said feed stream through said catalyst composition; passing a purge gas selected from the group consisting of steam, $N_2$, He, and Ar through said catalyst composition; and passing a free oxygen containing gas through said catalyst composition, under such conditions as to substantially burn off carbonaceous deposits on said catalyst compositions.

17. A process in accordance with claim 1, wherein said at least one alkene is selected from the group consisting of propylene, butene-1, butene-2, and isobutene.

18. A process in accordance with claim 1, wherein said at least one alkene is recovered.

* * * * *